（12）United States Patent　　(10) Patent No.: US 10,064,694 B2
Connolly　　(45) Date of Patent: Sep. 4, 2018

(54) LOCKING MECHANISM FOR A MEDICAL DEVICE ASSEMBLY TRAY

(71) Applicant: Medtronic Vascular, Inc., Santa Rosa, CA (US)

(72) Inventor: Colm Connolly, Ballybrit (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 89 days.

(21) Appl. No.: 14/996,264

(22) Filed: Jan. 15, 2016

(65) Prior Publication Data

US 2016/0213441 A1　　Jul. 28, 2016

Related U.S. Application Data

(60) Provisional application No. 62/106,457, filed on Jan. 22, 2015.

(51) Int. Cl.
*B65D 45/20*　　(2006.01)
*A61B 50/33*　　(2016.01)
*A61B 50/00*　　(2016.01)
*A61B 50/30*　　(2016.01)

(52) U.S. Cl.
CPC .............. *A61B 50/33* (2016.02); *B65D 45/20* (2013.01); *A61B 2050/005* (2016.02); *A61B 2050/006* (2016.02); *A61B 2050/0058* (2016.02); *A61B 2050/3008* (2016.02); *A61B 2050/3009* (2016.02)

(58) Field of Classification Search
CPC .................. B45F 13/14; F16B 5/0064; A61B 2050/3009; A61B 2050/0058; A61B 50/33; B65D 45/16; B65D 55/04; B65D 11/188; B65D 2525/28; B65D 2525/281; B65D 2525/289; A61M 1/0277; B42F 13/14; B42F 13/0006; B42F 13/0002; B42F 13/0026; B42F 13/004; B42F 13/0046; B42F 13/0008; B42F 13/0093; B42F 9/00; Y10T 24/15
USPC ......... 206/487, 1.5; 24/437, 30.5 W; 383/69; 220/324, 4.24
See application file for complete search history.

(56) References Cited

U.S. PATENT DOCUMENTS

| | | | | |
|---|---|---|---|---|
| 2,696,058 A | * | 12/1954 | Beyer | B60R 13/105 40/204 |
| 4,018,911 A | * | 4/1977 | Lionetti | A61K 35/18 424/533 |
| 4,469,227 A | * | 9/1984 | Faust | A01N 1/02 206/526 |
| 4,892,189 A | * | 1/1990 | Kunimune | G11B 33/0438 206/232 |

(Continued)

FOREIGN PATENT DOCUMENTS

FR　　2118331 A5 *　　7/1972　.......... B65D 25/282

*Primary Examiner* — Anthony Stashick
*Assistant Examiner* — Mollie Impink
(74) *Attorney, Agent, or Firm* — Medler Ferro Woodhouse & Mills PLLC

(57) ABSTRACT

A tray for a medical device assembly includes a tray body, a tray lid, and a connector arm. The tray body and the tray lid each have a first surface, a plurality of walls extending from the first surface, and an open end opposite the first surface. The connector arm is coupled to the tray body or the tray lid, and has a first position that permits the separation of the tray body and tray lid, and a second position that couples the tray body to the tray lid.

16 Claims, 5 Drawing Sheets

(56) References Cited

U.S. PATENT DOCUMENTS

| | | | |
|---|---|---|---|
| 8,376,177 B2 * | 2/2013 | Castner | A45C 11/20 |
| | | | 206/561 |
| 8,584,849 B2 | 11/2013 | McCaffrey | |
| 2002/0040906 A1 * | 4/2002 | Hakim | A47J 36/027 |
| | | | 220/574.2 |
| 2007/0086839 A1 * | 4/2007 | Pollock | B42F 9/00 |
| | | | 402/64 |
| 2009/0045096 A1 * | 2/2009 | Knutson | B65D 25/04 |
| | | | 206/570 |
| 2013/0287476 A1 * | 10/2013 | Huang | B42F 13/36 |
| | | | 402/41 |

* cited by examiner

LOCKING MECHANISM FOR A MEDICAL DEVICE ASSEMBLY TRAY

CROSS-REFERENCE TO RELATED APPLICATIONS

This application claims priority under 35 U.S.C. § 119(e) to the benefit of the filing date of U.S. Provisional Application No. 62/106,457 filed Jan. 22, 2015, the contents of which are incorporated herein by reference in their entirety.

FIELD OF THE INVENTION

The present invention relates to trays for medical device assemblies, and methods of securing and maintaining the sterile integrity of these medical device assemblies while encased within such trays during transport and storage. More specifically, the present invention relates to a locking mechanism for medical device assembly trays.

BACKGROUND

Heart valves are sometimes damaged by disease or by aging, resulting in problems with the proper functioning of the valve. Heart valve replacement has become a routine surgical procedure for patients suffering from valve dysfunctions. Traditional open surgery inflicts significant patient trauma and discomfort, requires extensive recuperation times, and may result in life-threatening complications.

To address these concerns, efforts have been made to perform cardiac valve replacements using minimally-invasive techniques. In these methods, laparoscopic instruments are employed to make small openings through the patient's ribs to provide access to the heart. While considerable effort has been devoted to such techniques, widespread acceptance has been limited by the clinician's ability to access only certain regions of the heart using laparoscopic instruments.

Still other efforts have been focused upon percutaneous transcatheter (or transluminal) delivery of replacement cardiac valves to solve the problems presented by traditional open surgery and minimally-invasive surgical methods. In such methods, a valve prosthesis is compacted for delivery in a catheter and then advanced, for example through an opening in the femoral artery and through the descending aorta to the heart, where the prosthesis is then deployed in the valve annulus (e.g., the aortic valve annulus).

Valve prostheses are generally formed by attaching a bioprosthetic valve to a frame made of a wire or a network of wires. Such a valve prosthesis can be contracted radially to introduce the valve prosthesis into the body of the patient percutaneously through a catheter. The valve prosthesis can be deployed by radially expanding it once positioned at the desired target site.

To prepare such a valve prosthesis for implantation, the valve prosthesis can be initially provided in an expanded or uncrimped condition, then crimped or compressed around the distal tip of the catheter assembly. Various methods and devices are available for crimping the valve prosthesis onto the catheter's distal tip, which may include hand-held devices or tabletop devices, for example. Due to the bioprosthetic valve, the valve prosthesis often is not shipped loaded into the delivery catheter. Instead, many transcatheter valve prostheses must be loaded into the catheter assembly by hand at the treatment facility (e.g., operating room, catheterization laboratory) immediately prior to performance of the procedure. Such transcatheter valve prostheses and their delivery catheters are often shipped in a medical device assembly tray, which may include a reservoir such that the valve prostheses may be loaded into the delivery catheter while submerged in a liquid solution in the reservoir. However, other medical devices, such as catheters used for devices other than heart valve prostheses, renal denervation devices, and other medical devices may also be shipped in medical device assembly trays.

The delivery catheter and/or medical device is regularly placed within the medical device assembly tray in a sterile environment. The tray is packaged within a sterile pouch, the pouch is sealed, and one, or both, of the pouch's ends are then folded against the medical device assembly tray. The folded pouch is placed within a shipping container for storage, transport, and delivery to treatment facilities. Unfortunately, the bulky tray designs can interact with the folds of the pouch, creating a risk to the sterile barrier integrity of the delivery catheter and/or medical device. Additionally, current tray designs are not ergonomically designed and the bulky trays are difficult to handle and manipulate.

Accordingly, there is a need for an improved tray design to protect these complex medical device assemblies.

SUMMARY OF THE INVENTION

Embodiments hereof relate to a tray for a medical device assembly. The tray includes a tray body, a tray lid, and a connector arm. The tray body has a first surface, a plurality of walls extending from the first surface, and an open end opposite the first surface. The tray lid has a first surface, a plurality of walls extending from the first surface, and an open end opposite the first surface. The connector arm is coupled to the tray body or the tray lid, and has a first, open position that permits the separation of the tray body and tray lid, and a second, closed position that couples tray body to the tray lid.

In an embodiment, the tray includes a flange extending outwardly from one of the walls of the tray body, and a flange extending outwardly from one of the corresponding walls of the tray lid. These corresponding flanges are in contact with each other when the tray lid is fitted over the tray body. The connector arm includes a cavity that is aligned with the flanges when the tray lid is fitted to the tray body. In the first, open position, the corresponding flanges are not disposed within the cavity such that the tray body and tray lid may be separated. In the second, closed position, the corresponding flanges are disposed within the cavity of the connector arm to retain the tray body and the tray lid together.

The connector arm may be rounded and/or cushioned.

DETAILED DESCRIPTION

Specific embodiments of the present invention are now described with reference to the figures, wherein like reference numbers indicate identical or functionally similar elements.

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

In an embodiment shown in FIGS. 1-5, a medical device assembly tray 200 includes connector arms 100, 101. Medical device assembly tray 200 is configured to be used with a catheter assembly (not shown). Other embodiments of the medical device assembly tray and connector arm are possible. Medical device assembly tray 200, described in greater detail below, is merely an exemplary embodiment of a medical device assembly tray and modifications can be made to the embodiments described herein without departing from the spirit and scope of the present invention. Therefore, the following detailed description is not meant to be limiting. Further, the systems and functions described below can be implemented in many different embodiments of hardware. Any actual hardware described is not meant to be limiting. The operation and behavior of the systems and methods presented are described with the understanding that modifications and variations of the embodiments are possible given the level of detail presented.

In the embodiment shown in FIGS. 1-5, medical device assembly tray 200 includes a first portion or tray body 202 and a second portion or tray lid 250. Connector arms 100 and 101 are coupled to tray body 202 such that connector arms 100 and 101 have a first, open position that will allow tray body 202 and tray lid 250 to be separated, and a second, closed position wherein tray body 202 and tray lid 250 are secured to each other.

Figure 1:
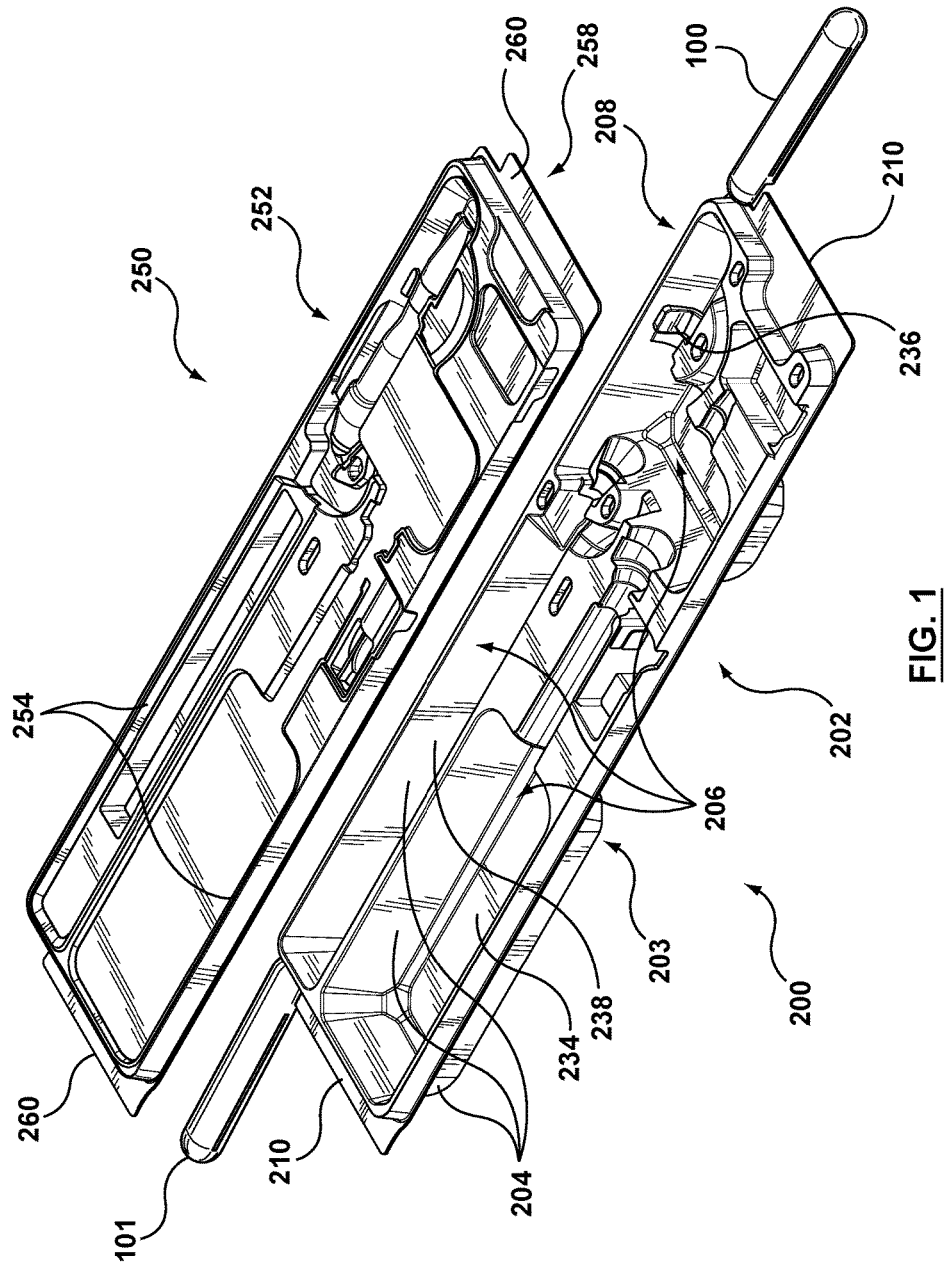
FIG. 1 is an exploded perspective view of a tray for a medical device assembly with a locking mechanism in accordance with an embodiment hereof.

As shown in FIG. 1, tray body 202 has a first or bottom surface 203 and a plurality of walls 204 extending upwardly from bottom surface 203. Spaces 206 between walls 204 define reservoirs and/or receptacles for parts of the medical device to be stored during shipment. In the embodiment shown, for example, tray body 202 defines a handle assembly receptacle 236 for seating a catheter handle assembly (not shown), an elongate delivery shaft receptacle 238 for seating a sheath assembly (not shown), and a reservoir 234 for holding a fluid (not shown). Other receptacles are also defined by walls and spaces of tray body 202. Tray body 202 further includes an open end 208 opposite first surface 203. Open end 208 generally defines an uppermost horizontal plane of tray body 202. Tray body 202 further includes flanges 210, extending outwardly from walls 204.

Tray lid 250 includes a first or top surface 252 defining a cover for tray body 202 and walls 254 extending downwardly from top surface 252. Walls 254 define spaces (not shown) between walls 254 matching spaces 206 of tray body 202 to further define the receptacles described above. The spaces of tray lid 250 are not shown in FIG. 1 because the spaces face tray body 202. An open end 258 is disposed opposite first surface 252. Tray lid 250 further includes flanges 260, extending outwardly from walls 254. Walls 254 and the spaces of tray lid 250 are generally sized and shaped to correspond to the receptacles of tray body 202 such that tray lid 250 covers the receptacles of tray body 202. As explained above, while the embodiment described herein shows specific configurations of walls 204, 254 and spaces 206, (not shown) of tray body 202 and tray lid 250, other configurations may be used to correspond to other configurations of tray 200 used for other devices.

Figure 2:
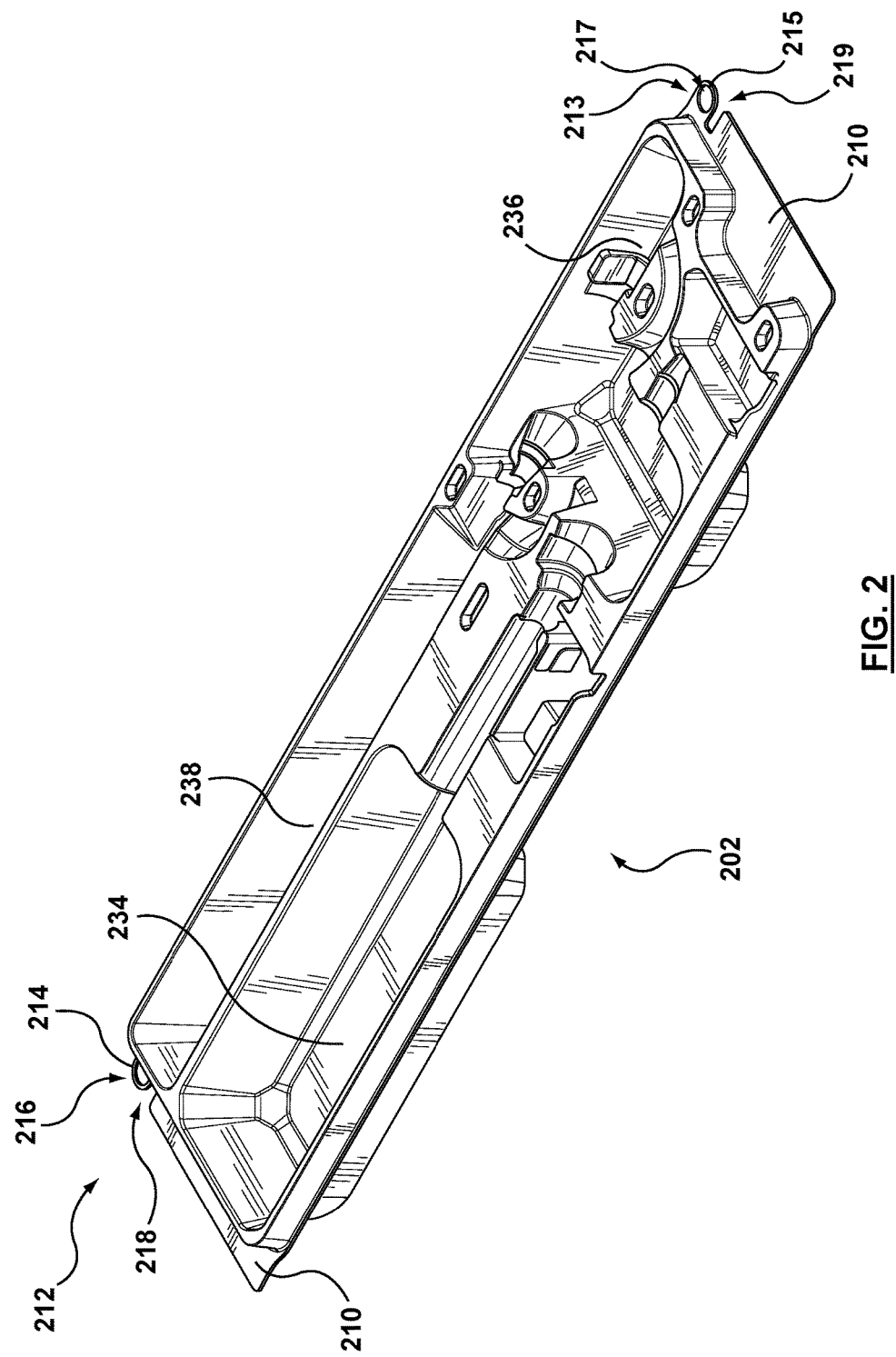
FIG. 2 is a perspective view of a tray body of the tray of FIG. 1 with the connector arms removed to expose the connector arm pivot points.

As shown in FIG. 2, tray body 202 further includes pivot mount points 212 and 213 for connector arms 100, 101 (described below). Each pivot mount point 212, 213 is an aperture 216, 217 through a pivot flange 214, 215, adjacent flange 210. In the embodiment shown in FIG. 2, a gap 218, 219 is disposed between flange 210 and pivot flange 214, 215 of its corresponding pivot mount point 212, 213. However, in other embodiments, flange 210 and pivot flange 214, 215 may be continuous. Pivot flange 214, 215 of its corresponding pivot mount point 212, 213 extends outwardly from a corresponding wall 204 and in the same plane as corresponding flange 210. Pivot mount points 212, 213 are generally located in a corner adjacent corresponding flange 210. Pivot mount points 212, 213 are configured to receive connector arms 100, 101 (described below) and to provide a point for connector arms 100, 101 to pivot between their first, open position and their second, closed position. Although pivot mount points 212, 213 are described as associated with tray body 202, they could instead be associated with tray lid 250.

Tray body 202 and tray lid 250 can be made of various polymer or composite materials including, for example, Polyethylene Terephthalate Glycol (PETG). The present invention, however, is not limited to polymer materials and can include other suitable materials, for example, composite materials or light weight sheet metal including aluminium or stainless steel. Tray body 202 and tray lid 250 can be manufactured with various processes including, not limited to, injection molding, cold press forming or thermoforming.

Other features of medical device assembly tray 200 shown in FIGS. 1-5 are not described in detail herein, but are explained in U.S. Pat. No. 8,584,849 to McCaffrey, which is incorporated in its entirety by reference herein. Further, as noted above, other medical device assembly trays with different shapes, receptacles, and surfaces may be used with the connectors arms described herein.

Connector arms 100, 101 are disposed in a corresponding pivot mount point 212/213 of tray body 202. Connector arms 100, 101 pivot in the same plane as flanges 210. While the embodiment of FIGS. 1-5 shows two corresponding connector arms 100 and 101, this is not meant to limit the invention, and more or fewer connector arms may be employed.

Figure 3:
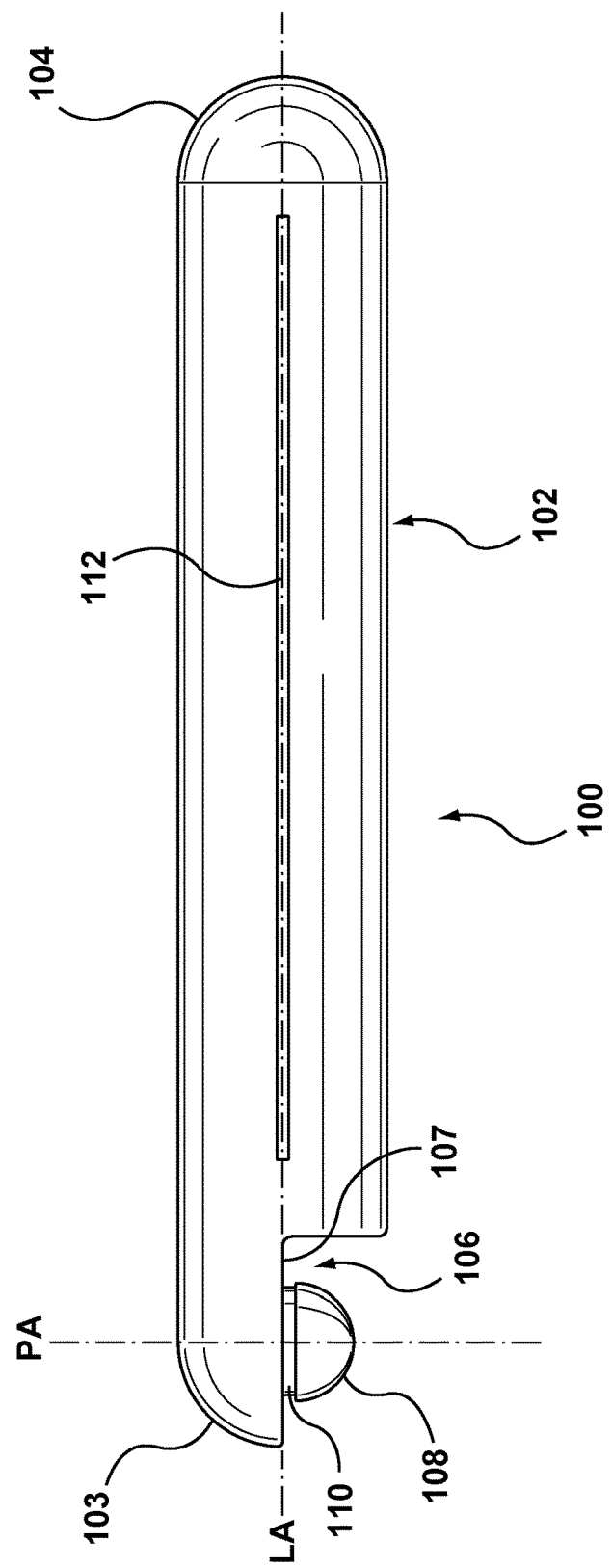
FIG. 3 is a schematic view of one of the connector arms of the tray of FIG. 1.

As shown in more detail in FIG. 3, connector arm 100 is an elongated arm having a body 102, a first end 103, and a second end 104. Although connector arm 100 is described with respect to FIG. 3, in the present embodiment, connector arm 101 is identical to connector arm 100. Accordingly, the description of connector arm 100 applies equally to connector arm 101.

A notch 106 is formed at the first end 103 of arm 100. Notch 106 is formed such that it creates a notch surface 107 that is aligned with and parallel to longitudinal axis LA of arm 100. A pivot retainer 108 is coupled to notch 106 at notch surface 107, Pivot retainer 108 extends from notch surface 107 perpendicular to longitudinal axis LA. A pivot axis PA is defined through pivot retainer 108 perpendicular to longitudinal axis LA. A pivot groove 110 extends circumferentially around pivot retainer 108 adjacent where pivot retainer 108 is coupled to notch surface 107. Pivot groove 110 defines a circumferential ring of a reduced diameter or channel such that pivot retainer 108 may be secured within and rotated within pivot mount point 212, as explained in more detail below. In other embodiments, notch surface 107 need not be aligned with longitudinal axis LA, but may be offset from longitudinal axis LA. For example, and not by way of limitation, notch surface 107 may be offset from longitudinal axis LA and pivot groove 110 may be spaced from notch surface 107 such that pivot groove 110 is aligned with longitudinal axis LA.

Distal of pivot groove 110 relative to notch surface 107, pivot retainer 108 is sized to be slightly larger in diameter than aperture 216 of pivot mount point 212 of tray body 202. Thus, in order to secure connector arm 100 to pivot mount point 212, pivot retainer 108 is pressed through aperture 216 of pivot mount point 212. Due to pivot retainer 108 being slightly larger in diameter than aperture 216, sufficient force is required to pass pivot retainer 108 through aperture 216 until reduced diameter pivot groove 110 is aligned with pivot flange 214 defining aperture 216. With pivot groove 110 aligned with pivot flange 214, pivot retainer 218 will not readily pass back through aperture 216 without an externally applied force. Pivot retainer 108, once pressed through pivot mount point 212, will couple and retain connector arm 100 to tray body 202 at pivot mount point 212. While FIG. 3 shows pivot retainer 108 as a hemisphere, it may be other shapes.

With pivot retainer 108 disposed through aperture 216 and pivot groove 110 aligned with flange 214, connector arm 100 can rotate about pivot axis PA. Such rotation about pivot axis PA allows connector arm 100 to pivot between a first, open position to a second, closed position. While this embodiment shows connector arm 100 with a press-fit or snap-fit method of attachment to tray body 202, this is not meant to limit the invention, and other methods of securing connector arm 100 may be employed.

Additionally, as shown in FIG. 3, connector arm 100 further includes a cavity 112, extending between first end 103 and second end 104. Cavity 112 extends along the longitudinal axis LA of arm 100. While FIG. 3 shows cavity 112 extending completely through the width of arm 100, forming a passage through arm 100, it is not meant to limit the design of arm 100, and cavity 112 may only extend partially though arm 100. Cavity 112 is configured such that, when connector arm 100 is coupled to tray body 202, cavity 112 is in the same plane as corresponding flange 210. Cavity 112 has a height (i.e., perpendicular to longitudinal axis LA) so as to allow corresponding flange 210 from tray body 202 and corresponding flange 260 from tray lid 250 to fit within cavity 112 when connector arm 100 is in the second, closed position, thereby securing tray lid 250 to tray body 202. Although cavity 112 has been described as aligned with longitudinal axis LA, cavity 112 could be parallel with and offset from longitudinal axis LA. Cavity 112 is aligned with flanges 210, 260 such that in the closed position described below, cavity 112 captures flanges 210, 260 to retain flanges 210, 260 together.

Connector arm 100 can be made of various polymer or composite materials including, for example, Closed-cell EVA and Low Density Polyurethane. The present invention, however, is not limited to polymer materials and can include other suitable materials, for example, silicone rubber, polystyrene or polychloroprene.

Connector arm 100 may further include a cushioned surface (not shown), the cushioning provided by either the material from which connected arm 100 is made or the cushion material being applied to the external surface of connector arm 100. The cushioned surface can provide a more ergonomic handle for the medical device assembly tray 200 and can also provide shock damage resistance and during handling of the medical device assembly tray 200. The cushioning material may be of various materials including, for example, Styrofoam or felt. The present invention, however, is not limited to these cushioning materials and can include other suitable materials, for example, natural sponge, silicone rubber or polychloroprene.

In the embodiment shown in FIG. 3, connector arm 100 is shaped as a cylinder with hemispherical rounded ends at first end 103 and second end 104. When medical device assembly tray 200 is transported and stored, it resides within a polymer pouch assembly (not shown) to maintain sterility of medical device assembly tray 200. A rounded body and ends 103, 104 of connector arms 100, 101 assist in preventing chaffing of the sterile pouch (not shown) and loss of sterility due to damage to the pouch. While the present embodiment shows connector arm 100 with a cylindrical body with hemispherical ends, it is not meant to limit the invention to this shape and other suitable shapes may be used within the spirit and scope of the invention.

Figure 4:
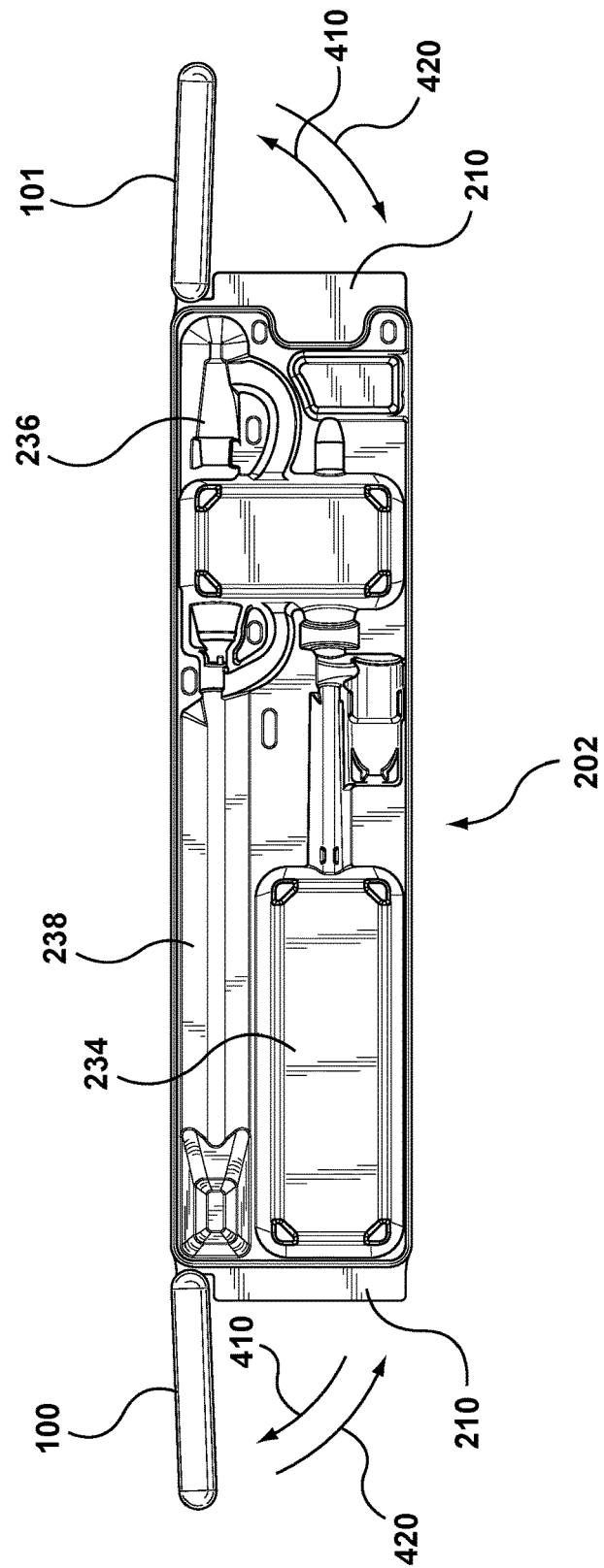
FIG. 4 is a top view of the tray body of the tray of FIG. 1 with the connector arms in the first, open position.

FIG. 4 shows a top view of tray body 202 with connector arms 100, 101 in the first, open position. As shown, arms 100, 101 are rotated away from corresponding flange 210 as shown by arrows 410. While arms 100, 101 are shown in a nearly perpendicular position to flange 210, the first, open position may be any position of arms 100, 101 in which tray body 202 may be separated from tray lid 250.

Figure 5:
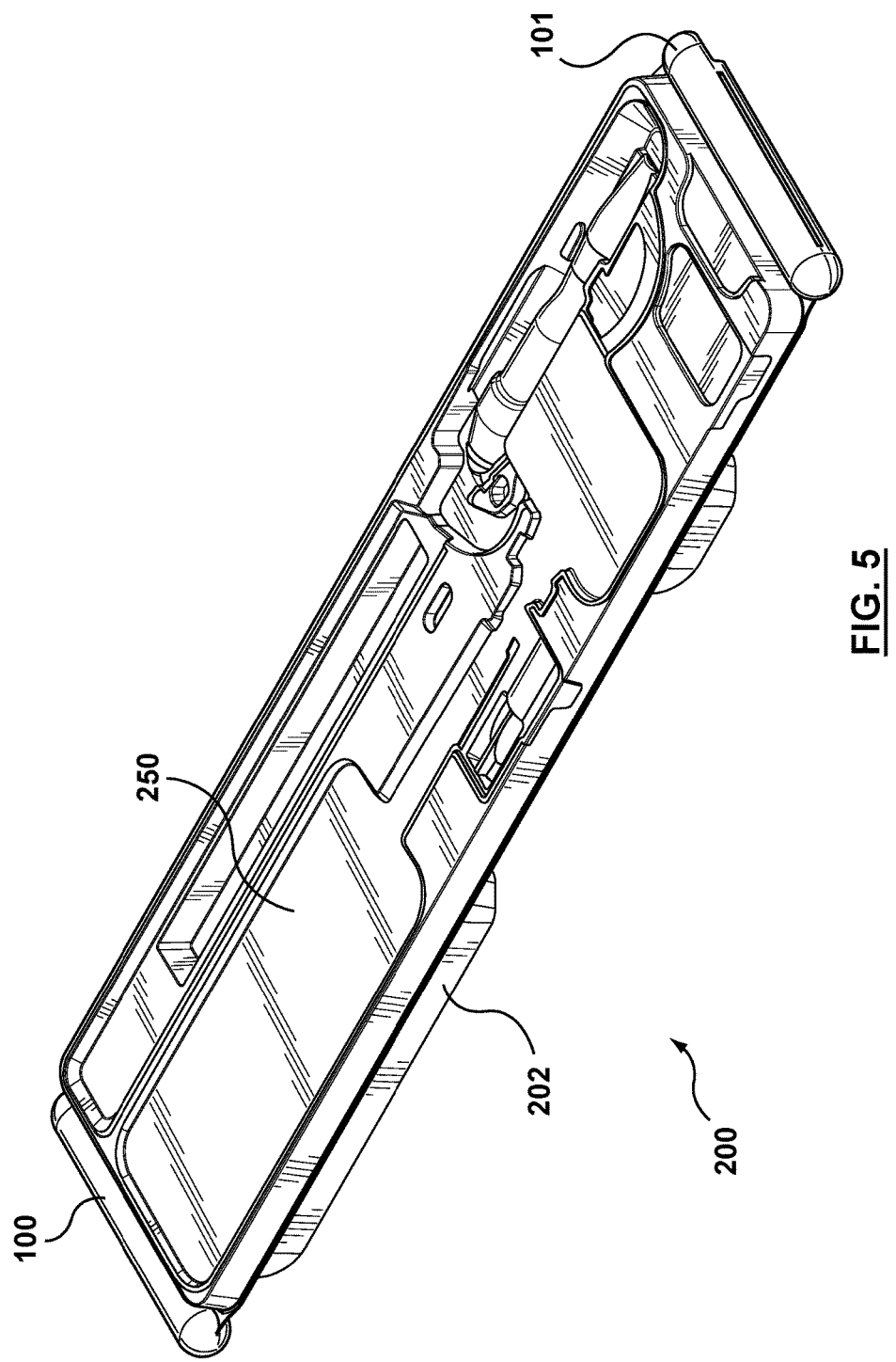
FIG. 5 is a perspective view of the tray of FIG. 1 with the connector arms in the second, closed position.

In order to couple tray lid 250 to tray body 202, tray lid 250 is placed over tray body 202 such that lid flange 260 aligns with flange 210 of tray body 202. Further, walls 254 and spaces of tray lid 250 align with corresponding walls 204 and spaces 206 of tray body. Then, connector arms 100, 101 are rotated towards corresponding flanges 210, 260, as shown by arrows 420 in FIG. 4, thereby capturing flanges 210, 260 within cavity 112 of corresponding connector arms 100, 101. FIG. 5 shows a perspective view of tray assembly 200, with tray lid 250 fitted to tray body 202, and with flange 210 and lid flange 260 residing within cavity 112 of corresponding connector arm 100, 101. Connector arms 100, 101 are in the second, closed position, coupling tray lid 260 to tray body 202.

While only some embodiments have been described herein, it should be understood that it has been presented by way of illustration and example only, and not limitation. Various changes in form and detail can be made therein without departing from the spirit and scope of the invention, and each feature of the embodiment discussed herein, and of each reference cited herein, can be used in combination with the features of any other embodiment. All patents and publications discussed herein are incorporated by reference herein in their entirety.

What is claimed is:

1. A tray for a medical device assembly, the tray comprising:
   a first portion comprising a first portion first surface, a plurality of first portion walls extending from the first portion first surface, and a first portion open end opposite the first portion first surface, wherein the plurality of first portion walls define a plurality of first spaces;
   a second portion configured to fit over the first portion having a second portion first surface, a plurality of second portion walls extending from the second portion first surface, and a second portion open end opposite the second portion first surface, wherein the plurality of second portion walls define a plurality of second spaces corresponding to the plurality of first spaces of the first portion;

a first connector arm coupled to the first portion or the second portion, wherein the first connector arm has a first position adapted to permit the separation of the first portion from the second portion of the tray, and a second position adapted to couple the first portion and the second portion together, wherein the first connector arm rotates in a first plane substantially parallel to the first portion first surface such that the first connector arm is in the first plane in both the first position and the second position;

a second connector arm coupled to the first portion or the second portion, wherein the second connector arm has a first position adapted to permit the separation of the first portion from the second portion of the tray, and a second position adapted to couple the first portion and the second portion together, wherein the second connector arm rotates in a second plane substantially parallel to the first portion first surface such that the first connector arm is in the second plane in both the first position and the second position, wherein the plurality of first spaces and the plurality of second spaces corresponding to the plurality of first spaces define a plurality of corresponding spaces which comprise a first corresponding space sized and shaped to receive a catheter handle therein, a second corresponding space sized and shaped to receive a catheter shaft therein, and a third corresponding space sized and shaped to hold a liquid, wherein the first connector arm and the second connector arm are disposed on opposite sides of the tray such that when each is in the first position, the first portion is configured to completely separate from the second portion, and wherein the first connector arm and the second connector are each pivotably connected to the first portion or second portion such that the first and second connector arms can pivot between the first position and the second position.

2. The tray of claim 1, wherein the first portion further comprises a first outwardly extending first portion flange extending from a first one of the first portion walls and a second outwardly extending first portion flange extending from a second one of the first portion walls, and wherein the second portion further comprises a first outwardly extending second portion flange extending from one of the second portion walls and a second outwardly extending second portion flange extending from a second one of the second portion walls, wherein the first outwardly extending first portion flange corresponds to the first outwardly extending second portion flange and the second outwardly extending first portion flange corresponds to the second outwardly extending second portion flange.

3. The tray of claim 2, wherein the first outwardly extending first portion flange and the first outwardly extending second portion flange are in contact with each other with the second portion fitted over the first portion of the tray, and wherein the second outwardly extending first portion flange and the second outwardly extending second portion flange are in contact with each other with the second portion fitted over the first portion of the tray.

4. The tray of claim 2, wherein the first connector arm has a first cavity and the second connector arm has a second cavity.

5. The tray of claim 4, wherein the first cavity in the first connector arm is in a first common plane as the first outwardly extending first portion flange and the first outwardly extending second portion flange with the second portion fitted over the first portion of the tray, and wherein the second cavity in the second connector arm is in a second common plane as the second outwardly extending first portion flange and the second outwardly extending second portion flange with the second portion fitted over the first portion of the tray.

6. The tray of claim 5, wherein the first outwardly extending first portion flange and the first outwardly extending second portion flange are both disposed within the first cavity of the first connector arm with the second portion fitted over the first portion of the tray and the first connector arm in the second position.

7. The tray of claim 1, wherein the first connector arm further comprises a first cushioned surface and the second connector arm further comprises a second cushioned surface.

8. The tray of claim 1, wherein the first connector arm further comprises rounded edges facing outwardly from a center portion of the tray with the first connector in the second position, and wherein the second connector arm further comprises rounded edges facing outwardly from the center portion of the tray with the second connector in the second position.

9. The tray of claim 1, wherein the first plane and the second plane are the same plane.

10. A tray for a medical device assembly, the tray comprising:

a first portion comprising a first portion first surface, a plurality of first portion walls extending from the first portion first surface, a first portion open end opposite the first surface, a first portion first flange extending outwardly from a first one of the plurality of first portion walls, and a first portion second flange extending outwardly from a second one of the plurality of first portion walls, wherein the plurality of first portion walls define a plurality of first spaces; and a second portion configured to fit over the first portion having a second portion first surface, a plurality of second portion walls extending from the second portion first surface, a second portion open end opposite the second portion first surface, a second portion first flange extending outwardly from a first one of the plurality of second portion walls, and a second portion second flange extending outwardly from a second one of the plurality of second portion walls, wherein the plurality of second portion walls define a plurality of second spaces corresponding to the plurality of first spaces of the first portion;

a first connector arm with a first cavity coupled to the first portion or the second portion, wherein with the second portion fit over the first portion such that the first portion first flange is aligned with the second portion first flange to define a first plane, the first connector arm has a first position such that the first portion first flange and second portion first flange are not disposed within the first cavity, and a second position adapted to retain the first portion first flange and the second portion first flange within the first cavity, wherein the first connector moves between the first and second positions in the first plane; and a second connector arm with a second cavity coupled to the first portion or the second portion, wherein with the second portion fit over the first portion such that the first portion second flange is aligned with the second portion second flange to define a second plane, the second connector arm has a first position such that the first portion second flange and second portion second flange are not disposed within the second cavity, and a second position adapted to retain the first portion second flange and the second portion second flange within the second cavity, wherein the second connector moves between the first and second positions in the second plane, wherein the plurality of first spaces and the plurality of second spaces corresponding to the plurality of first spaces define a plurality of corresponding spaces which comprise a first corresponding space sized and shaped to receive a catheter handle therein, a second corresponding space sized and shaped to receive a catheter shaft therein, and a third corresponding space sized and shaped to hold a liquid, wherein the first connector arm and the second connector arm are disposed on opposite sides of the tray such that when each is in the first position, the first portion is configured to completely separate from the second portion, and wherein the first connector arm and the second connector are each pivotably connected to the first portion or second portion such that the first and second connector arms can pivot between the first position and the second position.

11. The tray of claim 10, wherein the first portion or the second portion includes a first pivot mount point including a first aperture extending therethrough, wherein the first connector arm includes a first pivot retainer extending through the first aperture to couple the first connector arm to the first portion or the second portion, and wherein the first portion or the second portion includes a second pivot mount point including a second aperture extending therethrough, wherein the second connector arm includes a second pivot retainer extending through the second aperture to couple the second connector arm to the first portion or the second portion.

12. The tray of claim 11, wherein the first connector arm includes a first notch adjacent the first pivot retainer such that the first pivot retainer extends perpendicular to the first cavity from a first notch surface of the first notch, wherein the first notch surface is parallel to the first cavity, and wherein the second connector arm includes a second notch adjacent the second pivot retainer such that the second pivot retainer extends perpendicular to the second cavity from a second notch surface of the second notch, wherein the second notch surface is parallel to the second cavity.

13. The tray of claim 10, wherein the first cavity in the first connector arm is in the same plane as the first portion first flange and the second portion first flange with the second portion fitted over the first portion of the tray, and wherein the second cavity in the second connector arm is in the same plane as the first portion second flange and the second portion second flange with the second portion fitted over the first portion of the tray.

14. The tray of claim 10, wherein the first connector arm further comprises a first cushioned surface and the second connector arm further comprises a second cushioned surface.

15. The tray of claim 10, wherein the first connector arm further comprises rounded edges facing outwardly from a center portion of the tray with the first connector in the second position, and wherein the second connector arm further comprises rounded edges facing outwardly from the center portion of the tray with the second connector in the second position.

16. The tray of claim 10, wherein the first plane and the second plane are the same plane.

* * * * *